(12) United States Patent
Pfützenreuter et al.

(10) Patent No.: US 9,621,683 B2
(45) Date of Patent: *Apr. 11, 2017

(54) TRANSCODING OF COMMUNICATION WITH PERSONAL HEALTH DEVICES

(71) Applicant: Signove Tecnologia S/A, Campina Grande, Paraiba (BR)

(72) Inventors: Elvis Pfützenreuter, Prata (BR); José Luís do Nascimento, Campina Grande (BR); Mateus Assis Máximo de Lima, Campina Grande (BR)

(73) Assignee: Signove Tecnologia S/A, Campina Grande, Paraiba (BR)

(*) Notice: Subject to any disclaimer, the term of this patent is extended or adjusted under 35 U.S.C. 154(b) by 0 days.

This patent is subject to a terminal disclaimer.

(21) Appl. No.: 14/918,192

(22) Filed: Oct. 20, 2015

(65) Prior Publication Data

US 2016/0044141 A1 Feb. 11, 2016

Related U.S. Application Data

(63) Continuation of application No. 13/683,914, filed on Nov. 21, 2012.

(51) Int. Cl.
*H04L 29/06* (2006.01)
*H04L 29/08* (2006.01)
*G06F 19/00* (2011.01)

(52) U.S. Cl.
CPC ............ *H04L 69/08* (2013.01); *H04L 67/08* (2013.01); *H04L 67/2823* (2013.01); *H04L 67/2861* (2013.01); *G06F 19/3418* (2013.01)

(58) Field of Classification Search
None
See application file for complete search history.

(56) References Cited

U.S. PATENT DOCUMENTS

2012/0095393 A1* 4/2012 Reinke ............... G06F 19/3462
604/66
2012/0165728 A1* 6/2012 Strickland ........... G06F 19/3406
604/66

(Continued)

*Primary Examiner* — Hassan Phillips
*Assistant Examiner* — Duc Duong
(74) *Attorney, Agent, or Firm* — Schwabe, Williamson & Wyatt, P.C.

(57) ABSTRACT

In embodiments, devices, computer-readable media, and methods for personal health device transcoding may be described. A transcoding module may serve as an interface between a manager device implementing an IEEE 11073-20601 ("IEEE 11073") standard and a personal health device that does not implement the standard. The transcoding module may be configured to interact with one or more models of an IEEE 11073 stack implemented by the manager device. The transcoding device may be configured to redirect requests from the models and emulate responses from the personal health device such that the personal health device appears, to the manager device, to implement the IEEE 11073 standard. The transcoding module may perform the emulation asynchronously, through transcoding of communications with the personal health device, or may synchronously generate responses on behalf of the personal health device. Other embodiments may be described.

19 Claims, 8 Drawing Sheets

(56) References Cited

U.S. PATENT DOCUMENTS

| | | | | |
|---|---|---|---|---|
| 2013/0102853 A1* | 4/2013 | Halvorson | ............ | G06F 19/3418 600/300 |
| 2013/0235795 A1* | 9/2013 | Huang | .................. | H04W 28/18 370/328 |
| 2014/0107449 A1* | 4/2014 | Ecoff | .................. | A61B 5/0015 600/365 |
| 2015/0079908 A1* | 3/2015 | Schmitt | .................. | A61B 5/002 455/41.2 |

* cited by examiner

TRANSCODING OF COMMUNICATION WITH PERSONAL HEALTH DEVICES

CROSS-REFERENCE TO RELATED APPLICATIONS

This application is a continuation of and claims the benefit of the filing date of U.S. application Ser. No. 13/683,914, filed Nov. 21, 2012, entitled "TRANSCODING OF COMMUNICATION WITH PERSONAL HEALTH DEVICES," the disclosure of which is incorporated herein in their entirety.

BACKGROUND

Devices that communicate with each other, such as over a network, may often make use of interfaces or protocols that may define or describe types and/or formats of data that may be exchanged between the devices. One such set of interfaces may be defined by the IEEE 10703-20601 standard ("IEEE 11073"), which is a standard for personal health devices. Such devices may include, but are not limited to, for example, weighing scales, blood pressure measurement devices, glucose meters, heart rate monitors, etc. These devices may be employed in non-intensive care conditions, such as at a patient's home or while exercising. The standard describes a stack of protocols as well as roles taken by sensor and collector devices.

A personal health device, such as a sensor device, may take an agent role in IEEE 11073. A manager device may perform data collection activities in IEEE 11073. In various implementations, IEEE 11073 may put larger processing burden on manager devices, allowing agents typically to possess more limited processing power and/or lesser power requirements. Managers, by contrast may be executed in relatively more powerful apparatuses. These apparatuses may include various devices such as, but not limited to, mobile devices, cell phones, desktop computer, laptops computers, and/or servers.

However, there are many personal health devices in the market that do not follow IEEE 11073. There may be various reasons for this, including that some kinds of personal health devices simply cannot afford to fully implement an IEEE 11073 agent role. For example, some personal health devices may be expected to have a very long battery life or to be very simple in nature. This may lead to devices that have ultra-low power requirements, minuscule processing power, and/or severe restrictions on data transmission and reception.

In the other hand, IEEE 11073 may be increasingly important in the personal health devices market as larger numbers of compliant devices and managers are used. It may therefore be desirable to facilitate connection of non-IEEE 11073-compliant personal health devices to IEEE 11073 managers.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

In the following detailed description, reference is made to the accompanying drawings which form a part hereof wherein like numerals designate like parts throughout, and in which is shown by way of illustration embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

As used herein, the term "module" may refer to, be part of, or include an Application Specific Integrated Circuit ("ASIC"), an electronic circuit, a processor (shared, dedicated, or group) and/or memory (shared, dedicated, or group) that execute one or more software or firmware programs, a combinational logic circuit, and/or other suitable components that provide the described functionality.

Figure 1:
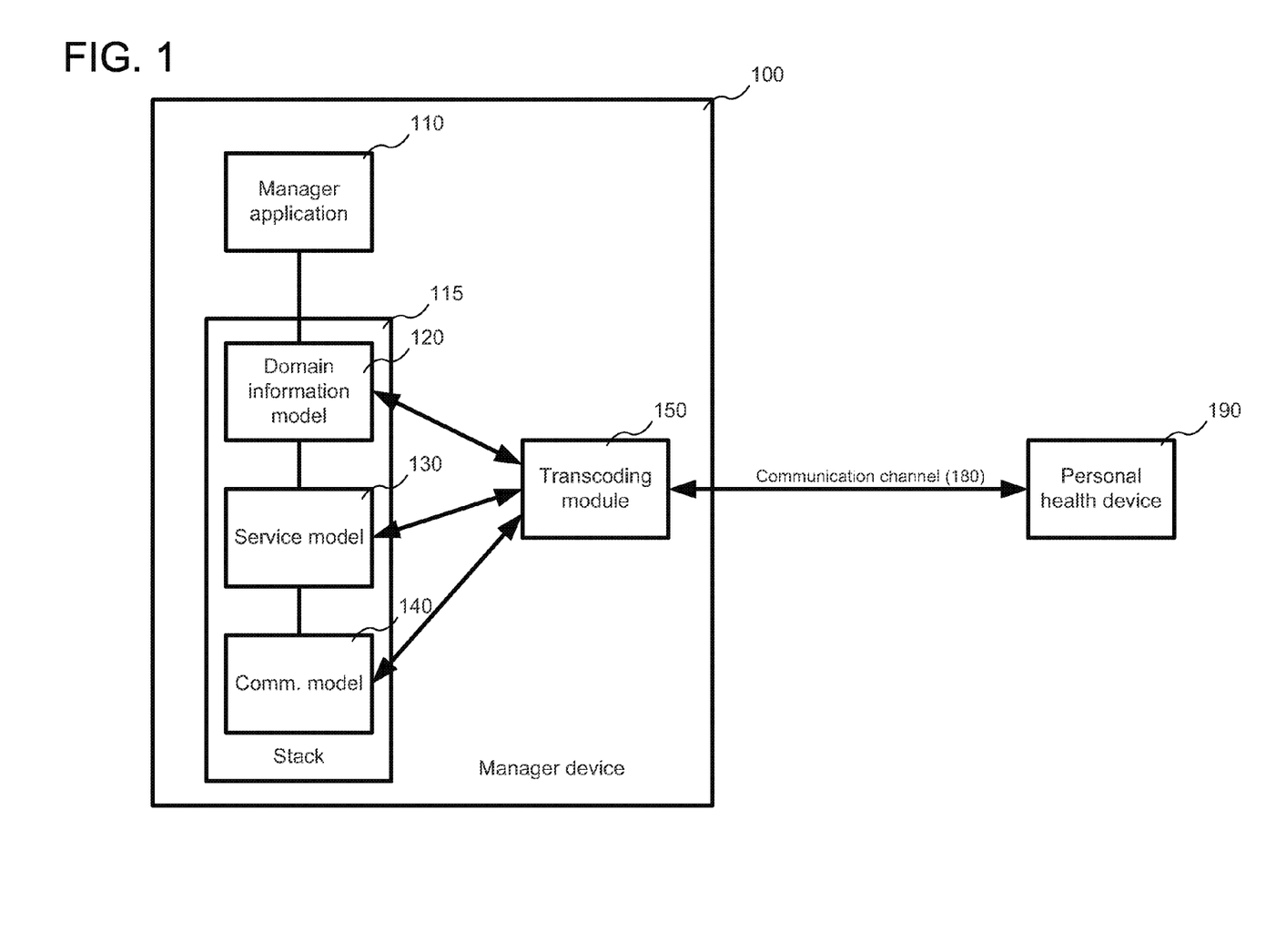
FIG. 1 is a block diagram illustrating example components used in personal health device transcoding, in accordance with various embodiments.

Referring now to FIG. 1, a manager device 100 is shown according to various embodiments. In various embodiments, the various components and modules illustrated in FIG. 1 may be combined, broken into sub-components, and/or omitted entirely. The manager device 100 may communicate with a personal health device 190, such as to control the personal health device 190 and/or to receive data from the personal health device 190. In various embodiments, the communication may be performed via a communication channel 180; the communication channel may include one of various wired and/or wireless communication channels, including Bluetooth™, WiFi, Ethernet, and/or RF channels.

In various embodiments, the manager device 100 may implement the IEEE 11073 standard. In various embodiments, the 11073 standard may specify various models that form a stack of protocols 115, through which a manager application 110 may attempt to communicate with various personal health devices, such as personal health device 190. As illustrated, the manager device 100 may include a stack of three layered models: a communication model 120, a service model 130, and a domain information model 140. In various embodiments, the models 120-140 may be implemented through different means, such as, for example, using software and/or hardware modules. In various embodiments, the models of the stack 115 may map roughly to an Open Systems Interconnection ("OSI") network model as follows: the communication model 140 may map to transport and presentation layers of an OSI model; the service model may map to a session layer of an OSI model; and the domain information model may maps to an application layer of an OSI model.

The manager device 100 may also include a transcoding module 150. In various embodiments, the transcoding module 150 may be configured to facilitate communication between the manager device 100 (and specifically between the manager application 110) and the personal health device 190. In various embodiments, the transcoding module 150 may be configured to facilitate communications between the manager device 100 and the personal health device 190 even when the personal health device 190 does not implement IEEE 11073. Thus, in various embodiments, the transcoding module 150 may be configured to interact with the various models 120-140 of the stack 115 in order to redirect communications sent through the stack 115 and to emulate communication with the personal health device such that the device appears to implement IEEE 11073. In various embodiments, the transcoding module 150 may fill a role of collector/manager from the point of view of the personal health device 190 and may fill the role of an IEEE 11073 agent on behalf of the non-IEEE-11073-compliant personal health device 190, from the point of view of the manager device 100.

It may be noted that, while the transcoding module 150 is called a "transcoding module," this should not necessarily imply that in every embodiment the transcoding module 150 only performs transcoding of data received and sent to the personal health device 190. In various embodiments, the transcoding module 150 may perform transcoding of data sent to or from the personal health device 190. In other embodiments, however, the transcoding module 150 may emulate a communication as if the communication was received from the personal health device 190 without requiring that the personal health device 190 initiate the communication. Conversely, while the transcoding module 150 may be referred to as "emulating" communications between the manager device 100 and the personal health device 190, in various embodiments, this should not imply that any or all communications sent through the transcoding module 150 are not based on actual communications sent to or from the personal health device 190. In various embodiments, the transcoding module 150 may take actual data sent to or from the personal health device 190, may perform transcoding on that data, and may send the transcoded data on, facilitating actual communications between the manager device 100 and the personal health device 190.

In various embodiments, the transcoding module 150 may be configured to communicate in both "live" and "non-live" manners. Live transcoding may, in various embodiments, take place while the personal health device 190 is currently connected with the transcoding module 105 and while two-way, end-to-end communication between the manager device 100 and the personal health device 190 is possible. In various embodiments, the transcoding module may also be configured to perform non-live transcoding, which may store data from the personal health device 190 and then later make it available for the manager device 100.

In various embodiments, the transcoding module may include a running IEEE 11073 stack, similar to stack 115, that may take the role as an agent, and may communicate with the manager device 100 using its stack. In addition, the transcoding device may also include a second protocol stack that can communicate with the personal health device 190, such as via a non-IEEE 11073 protocol that is understood by the personal health device 190.

In various embodiments, however, the transcoding module 150 may be integrated into the implementation of the stack 115 of the manager device 100 such that the transcoding module 150 may avoid implementing an IEEE 11073 agent role.

Thus, in various embodiments, the transcoding module may implement the a protocol and state machine for the personal health device 190, and may establish one-to-one relationships between native device events and IEEE 11073 events. The transcoding module 150 may be configured to feed such events directly into the models 120-140 of the stack 115. Thus, as illustrated in FIG. 1, rather than communicate solely with the lowest level of the stack 115 (e.g., the communication model 140), the transcoding module 150 may communicate directly with various other models, such as the domain information model 120 and/or the service model 130. Further, while in some IEEE 11073 implementations application packet data units ("APDU"s) are transmitted for communication between manager devices and personal health devices, in various embodiments, at the communication model 140 level, the transcoding module 150 may be configured such that the communication model 140 does not communicate or receive application packet data units to or from the transcoded devices. Instead, these application packet data units may be redirected before reaching the communication model 140. In various embodiments, the transcoding module 150 may avoid the sending of APDUs because the transcoding module 150 may not operate as an IEEE 11073 agent. Thus, IEEE 11073 events that might result in the sending of an APDU may be rerouted by the transcoding module 150 for handling, such as described below. This rerouting may happen in different places of the stack 115 based on factors such as the event type.

In various embodiments, the transcoding module 150 may execute in the same device and/or processing unit other actions and modules of the manager device 110. Thus, in various embodiments, the transcoding module 150 may live in the same host and process space as the manager application 110 and the stack 115. The transcoding module may also shares memory with these components. In various embodiments, the transcoding module 150 may be implemented as a software plug-in, allowing easier and/or dynamic support addition to a new sensor devices model without changing the stack 115 itself. In various embodiments, manager device may include more than one transcoding module 150, such as for various different personal health devices 190. However, for the purposes of ease of illustration and description, only one transcoding module 150 and one personal health device 190 are shown and described.

Figure 2:
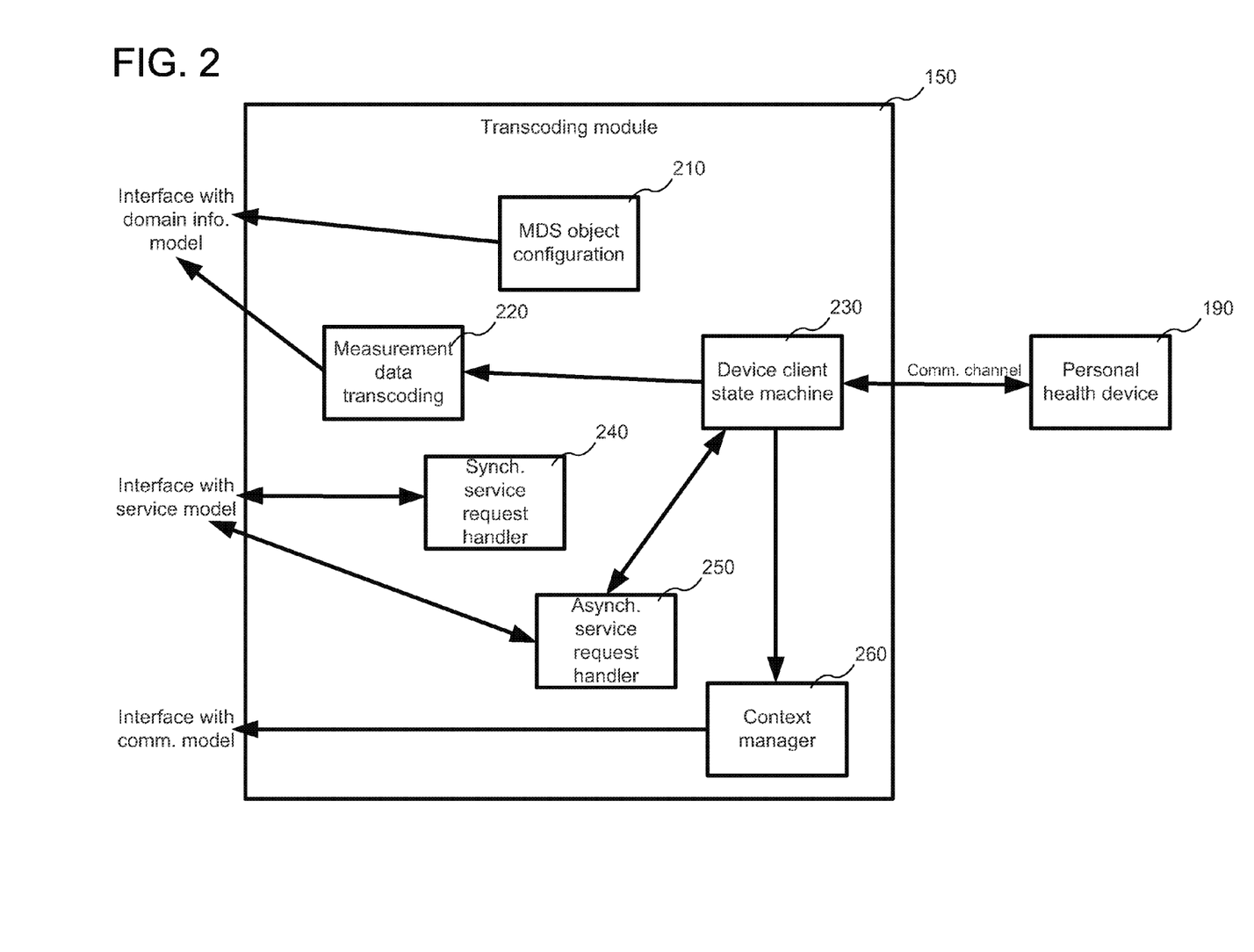
FIG. 2 illustrates an example of components found in a transcoding module, in accordance with various embodiments.

Referring now to FIG. 2, an example of components found in the transcoding module 150 is illustrated in accordance with various embodiments. As FIG. 2, illustrates, in various embodiments, the transcoding module may include various modules which may communicate with the personal health device 190 or with various level of the stack 115 of the manager device 100. In various embodiments, the various components and modules may be combined, broken into sub-components, and/or omitted entirely.

In various embodiments, the transcoding module 150 may communicate with the personal health device 190 through the device client state machine module 230. In various embodiments, the device client state machine module 230 may implement a collector side of the non-IEEE 11073-compliant protocol which is supported by the personal health device 190. In various embodiments, the device client state machine module 230 may also implement a state machine for the personal health device 190. In various embodiments, the device client state machine module 230 may be the component of the transcoding module 150 that communicates directly with the personal health device 190, while other modules communicate through the device client state machine module 230.

The transcoding module 150 may also include a context manager 260. In various embodiments, the context manager 260 may be configured to supply a connection context to the communication model 140 of the stack 115. In various embodiments, the context provided by the context manager 260 may uniquely represent the physical health device 190. In various embodiments, the context provided by the context manager 260 may be uniquely mapped to a unique system ID. In various embodiments, this unique mapping may facilitate the transcoding module 150 in allowing the stack 115 to handle both transcoded devices (e.g. the personal health device 190) and non-transcoded devices in a similar fashion throughout the stack.

In various embodiments, the transcoding module may include an MDS object configuration module 210. In various embodiments, the MDS object configuration module 210 may be configured to generate association and configuration information and to pass this information to the stack 115 such that the manager device 100 may create and populate a Medical Device System ("MDS") object to identify the personal health device and its status. The association and configuration information generated by the MDS object configuration module 210 may also identify one or more objects provided by the personal health device 190 to the manager device 100. In various embodiments, the MDS object configuration module 210 may provide the association information directly to the domain information model 120.

In various embodiments, the association information generated by the MDS object configuration module 210 may be based on actual information received from the personal health device 190 or may be generated entirely by the MDS object configuration module 210 without requiring information from the personal health device 190. Implementations of processes for the transcoding module 150 to share association information with the manager device 100 are described below.

The transcoding module 150 may also include a measurement data transcoding module 220, which may be configured, in various embodiments, to transcode measurement data received from the personal health device 190 by the device client state machine module 230 such that the data is compliant with IEEE 11073. In various embodiments, the measurement data transcoding module 220 may provide the association information directly to the domain information model 120.

The transcoding module 150 may also comprise a synchronous service request handler module 240 and an asynchronous service request handler 250. In various embodiments, these modules 240 and 250 may be configured to handle requests from, and to provide responses to, the service model 130 of the stack 115. As illustrated, in various embodiments, the synchronous service request handler 240 may be configured to receive and responds to requests without communicating with the personal health device 190. Also, as illustrated, in various embodiments, the asynchronous service request handler 250 may be configured to respond to requests by communicating with the personal health device 190 through the device client state machine module 230. Particular examples of responding to requests are discussed below.

Figure 3:
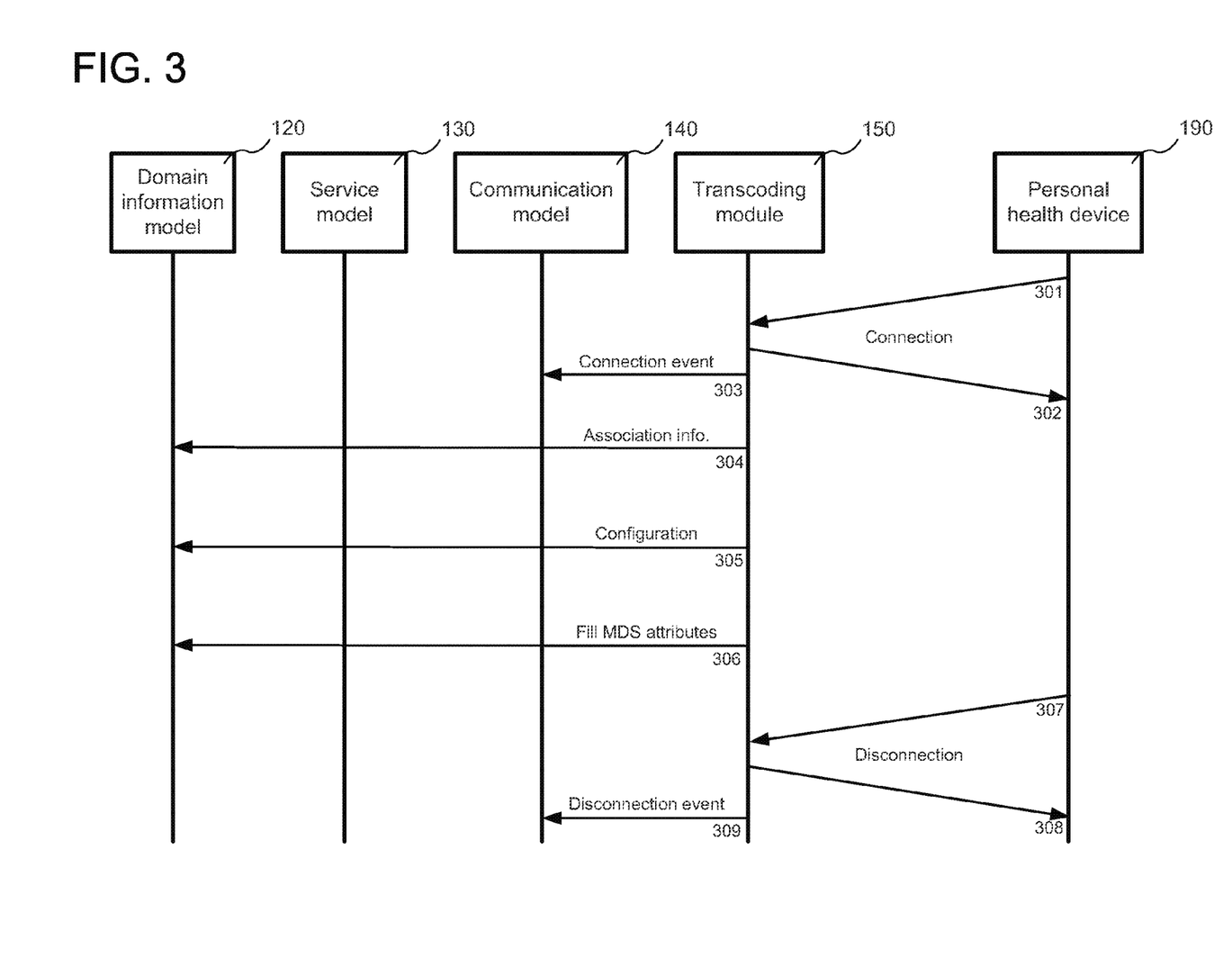
FIG. 3 illustrates an example personal health device connection, configuration, and disconnection process, in accordance with various embodiments.

FIG. 3 illustrates an example personal health device connection, configuration, disconnection process, in accordance with various embodiments. In various embodiments, the actions illustrated in FIG. 3 may be performed by the transcoding module 150 in order to form a connection between the manager device 100 and the personal health device 190, to provide association and configuration information to the manager device 100, and later to end the connection. In various embodiments, the action described in FIG. 3 may be merged, divided into other actions, and/or reordered. The process may begin at operation 301, where the transcoding module 150 may receive a connection request from the personal health device 190; the transcoding module 150 may respond to that request at operation 302, thus forming a connection between the transcoding module 150 and the personal health device 190. As discussed above, in various embodiments, the connection may be made by the device client state machine module 260 of the transcoding module 150, and communication between the personal health device 190 and the device client state machine module 260 may be performed using a protocol supported by the personal health device 190 and may be other than IEEE 11073. After establishment of the connection, then at operation 303 the transcoding module may sent a connection event to the communication model 140, to establish to the communication model 140 of the stack 115 that a connection has been opened. It may be noted that other communications may be not be sent to the communication model 140; instead, the communication model 140 may be bypassed in lieu of direct communication with the other models of the stack 115.

After establishment of the connection, at operation 304 the transcoding module 150 may provide association information to the domain information model 120. In various embodiments, the association information may be provide to the domain information model by the MDS object configuration module 210 of the transcoding module 150. As illustrated, in various embodiments, this association information may be provided directly to the domain information model 120 and may bypass other models in the stack, such as the communication model 140 and the service model 130. This association information may correspond to an IEEE 11073 association event. In various embodiments, the personal health device may not have a state similar to IEEE 11073 association; in such embodiments, the transcoding module 150 may generate the association information right after the connection event. This generation of the association information may thus be performed without communication with the personal health device 190, in various embodiments. Alternatively, if the personal health device 190's state machine prescribes some kind of protocol handshake before it can send actual measurement data (or otherwise be communicated with), the transcoding module 150 may, in various embodiments, send association information after performing a handshake process with the personal health device 190.

In various embodiments, at operation 304 the transcoding module may fill an IEEE 11073 PhdAssociationInformation structure and may pass it to the domain information module 120 of the stack 115. In various embodiments, the use of the PhdAssociationInformation may provide a balance between complexity in the transcoding module 150 and in adding complexity to the stack 115. It may be noted that the PhdAssociationInformation may be received in some IEEE 11073 managers in an association APDU. By using similar structures, various embodiments, may keep reduce distinctions between transcoded and non-transcoded devices from the perspective of the manager device 100.

In various IEEE 11073 manager device implementations, after receiving association information, an IEEE 11073 Manager may go from a "disassociated" to an "operating" state if a configuration for an IEEE 11073 Agent is already known. Otherwise, in IEEE 11073 implementations, the IEEE 11073 Manager may go to an "associated" state and may inform the associated IEEE 11073 Agent configuration information for the associated IEEE 11073 Agent (identified by information in the PhdAssociationInformation) is unknown. The IEEE 11073 Agent device is then be expected to send a ConfigReport APDU. Once the IEEE 11703 Manager receives the configuration and approves it, MDS objects may be created in the IEEE 11073 Manager's memory.

Thus, in order to provide interoperability with the personal health device 190, in various embodiments, at operation 305, the transcoding module 150 may provide configuration information to the domain information module 120. In various embodiments the provision of the configuration information may be provided after the stack 115 of the manager device 100 notifies the transcoding module 150 that the identified configuration is unknown. Thus, in various embodiments, the transcoding module 150, may fill a ConfigReport structure and send it to the domain information model 120 of the stack 115. This provisioning of the configuration information may be provided, in various embodiments, by the MDS object configuration module 210 of the transcoding module 150.

In various embodiments, the ConfigReport structure may be generated locally by the transcoding module 150 and may be generated with a higher likelihood of being error-free. Therefore, in various embodiments, the transcoding module 150 may assume that the stack 115 will not reject the configuration; the transcoding module 150 may therefore not receive (or expect) any further feedback. The transcoding module 150 may therefore operate under the assumption that, after the configuration information is provided, that the current context for the personal health device 190 is an "operating" state.

In various embodiments, at operation 306, MDS attributes in the domain information module 120 of the stack 115 may then be filled by the transcoding module 150. In various embodiments, the transcoding module 150 may fill the MDS attributes by directly writing to/changing an MDS structure in the domain information model 120 of the stack 115 of the manager device 100. In various embodiments, the transcoding module 150 may fill in the attributes without performing APDU encoding or a service request. In various embodiments, the filling of the MDS attributes may be performed by the MDS object configuration module 210 of the transcoding module 150. In various embodiments, attributes described in IEEE 11073 may be fulfilled. In some embodiments, all attributes that are mandated by IEEE 11073 may be filled, even those attributes that are not mapped to any feature in the personal health device 190.

In various embodiments, a disconnection of the personal health device 190 may also be facilitated by the transcoding module 150. Thus, at operation 307, the personal health device may send a disconnection notice to the transcoding module 150, and may receive an acknowledgement from the transcoding module 150. The transcoding module 150 may then generate an disassociation event for the connection context and send this to the communication model 140 of the stack 115. In various embodiments, if the personal health device 190 does not have a state similar to IEEE 11073 disassociation, the transcoding module may generate the disassociation event at operation 309 right before the disconnection with the personal health device 190. The process may then end.

Figure 4:
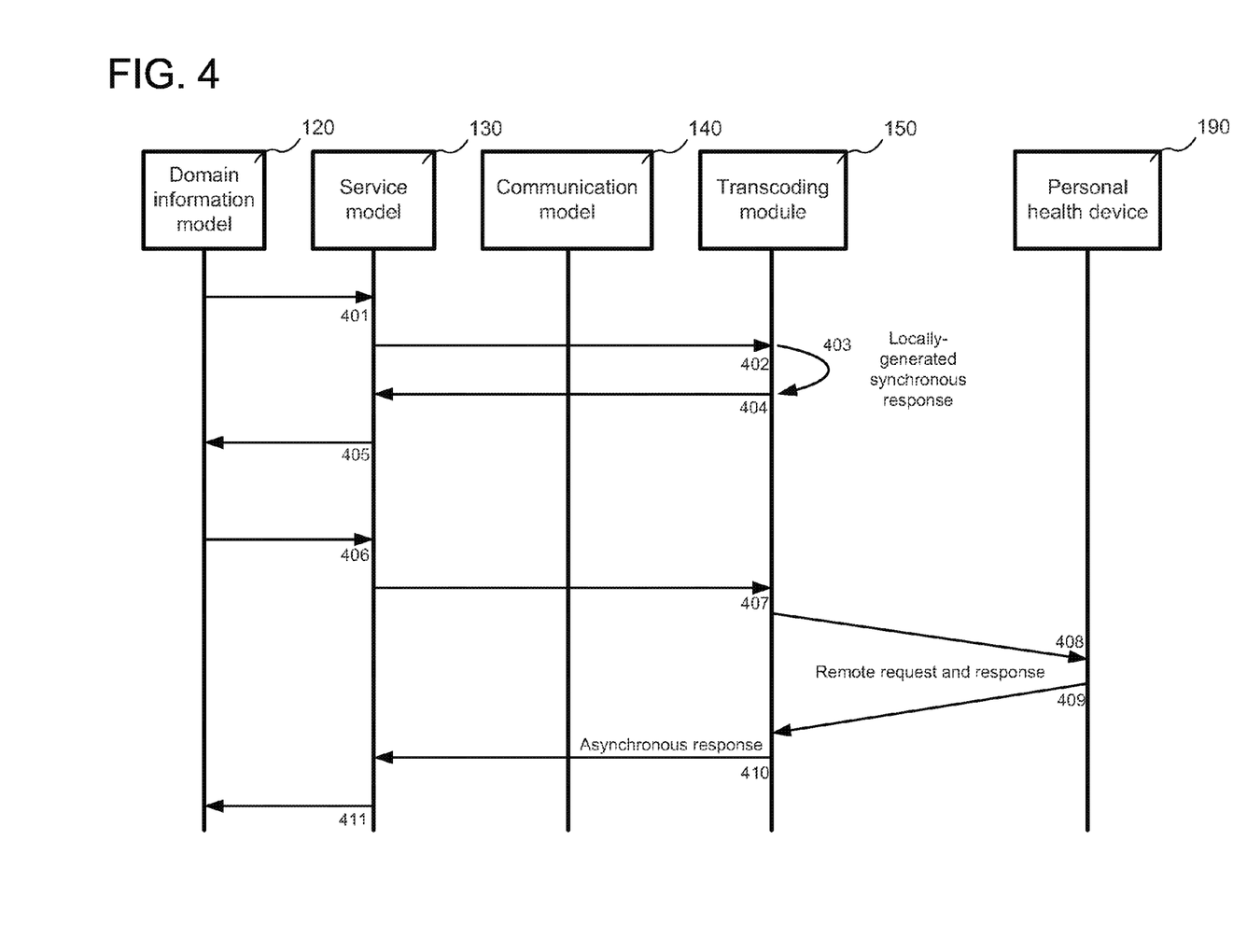
FIG. 4 illustrates example personal health device request and response processes, in accordance with various embodiments.

FIG. 4 illustrates example personal health device request and response processes, in accordance with various embodiments. In various embodiments, the actions illustrated in FIG. 4 may be performed by the transcoding module 150 in order to facilitate requests and responses between the manager device 100 and the personal health device 190. In various embodiments, the action described in FIG. 4 may be merged, divided into other actions, and/or reordered.

In various embodiments, the transcoding module 150 may provide service model-level transcoding with the personal health device 190. In various embodiments, requests from the manager device 100 to the personal health device 190 (serving the IEEE 11073 Agent role) are partially handled as IEEE 11073 service requests within the stack 115. However, in various embodiments, the service model 130 may be configured to distinguish between transcoded devices and devices that implement the IEEE 11073 Agent role on their own. The service model 130 may be configured to thereby reroute requests received from the domain information model 120 to the transcoding module instead of generating a remote operation invoke request APDU and sending the request to the communication model 140. In other embodiments, the service model may not distinguish between transcoded and non-transcoded devices. In some such embodiments, the transcoding module 150 may be configured to redirect a remote operation invoke request APDU generated by the service model without the service model 130 being aware of the transcoding module's interception.

In various embodiments, requests from the manager device 100 may be distinguished into two subtypes: synchronous and asynchronous. In various embodiments, synchronous requests may be fulfilled within the transcoding module 150, without need of communication with the personal health device 190. Thus, a synchronous request and response process may begin at operation 401, where, in various embodiments, the domain information model 120 may send a request to the service model 130. Next, at operation 402, in various embodiments the service model 130 may send the request to the transcoding module. At operation 403, in various embodiments the transcoding module 150 may generate a response locally without communicating with the personal health device 190. At operation 404, the locally-generated response may then, in various embodiments, be sent to the service model 130, and the service model 130 may send the response to the domain information model 120 at operation 405. The process may then end.

By contrast with synchronous requests, in various embodiments asynchronous requests may change the state of the state machine of the personal health device 190. The asynchronous response may, in various embodiments, be received from the personal health device 190 and then transcoded back to the service model 130. In various embodiments, the transcoding module 150 may be configured to keep track of the personal health device 190 and to notify the service model 130 with a negative response in case of failure. In various embodiments, the service model 130 may be configured to provide a hook for the transcoding module 150 to send positive or negative responses.

An asynchronous request and response process may begin at operation 406, where, in various embodiments, the domain information model 120 may send a request to the service model 130. Next, at operation 407, in various embodiments the service model 130 may send the request to the transcoding module. At operations 408 and 409, in various embodiments the transcoding module 150 may send the request to the personal health device 190 and may receive a response from the personal health device 190. At operation 410, the received response may then, in various embodiments, be sent to the service model 130, and the service model 130 may send the response to the domain information model 120 at operation 411. The process may then end.

In various embodiments, methods of classifying requests from the manager device 100 as synchronous or asynchronous may vary. In various embodiments, the manner of classification may vary based on the sets of features provided by various personal health devices 190, which may be mapped to MDS attributes in different ways. In one example, a transcoding module 150 may be configured to interoperate with a relatively simple personal health device 190 that is configured only to send measurement values using, for example, a simplex protocol. Such a transcoding module may be configured to handle service requests synchronously.

In various embodiments, the transcoding module 150 may be configured to handle Get and Set operation requests on MDS attributes from the stack 115 of the manager device 100. In various embodiments, the Get and Set operation requests may be handled synchronously or asynchronously based on, for example, capabilities of the personal health device 190 as well as whether these capabilities can be mapped to MDS attributes.

In various embodiments, a Set-Time operation request may be transcoded in an analog way. Thus, the transcoding module may, in various embodiments, fill relevant MDS attributes accordingly to Set-Time support. In various embodiments, the Set-Time operation request may be supported when the personal health device 190 has an internal and resettable clock. In other embodiments, the transcoder module 150 may be configured to maintain a clock separate from the manager device 100. Thus, measurement timestamping may be supported in various ways.

In various embodiments, requests from the personal health device to the manager device may not be transcoded as IEEE 11073 service requests. Instead, these requests may be fed directly and synchronously into the domain information model 120 (not illustrated). For example, as discussed above, during configuration, MDS attributes (such as, for example, supplied by the MDS object configuration component 210 of the transcoding module 150) may be provided directly to the domain information model 120. In other examples, in various embodiments, measurement data and store segment data (both supplied by measurement transcoding module) may be provided directly to the domain information model.

Figure 5:
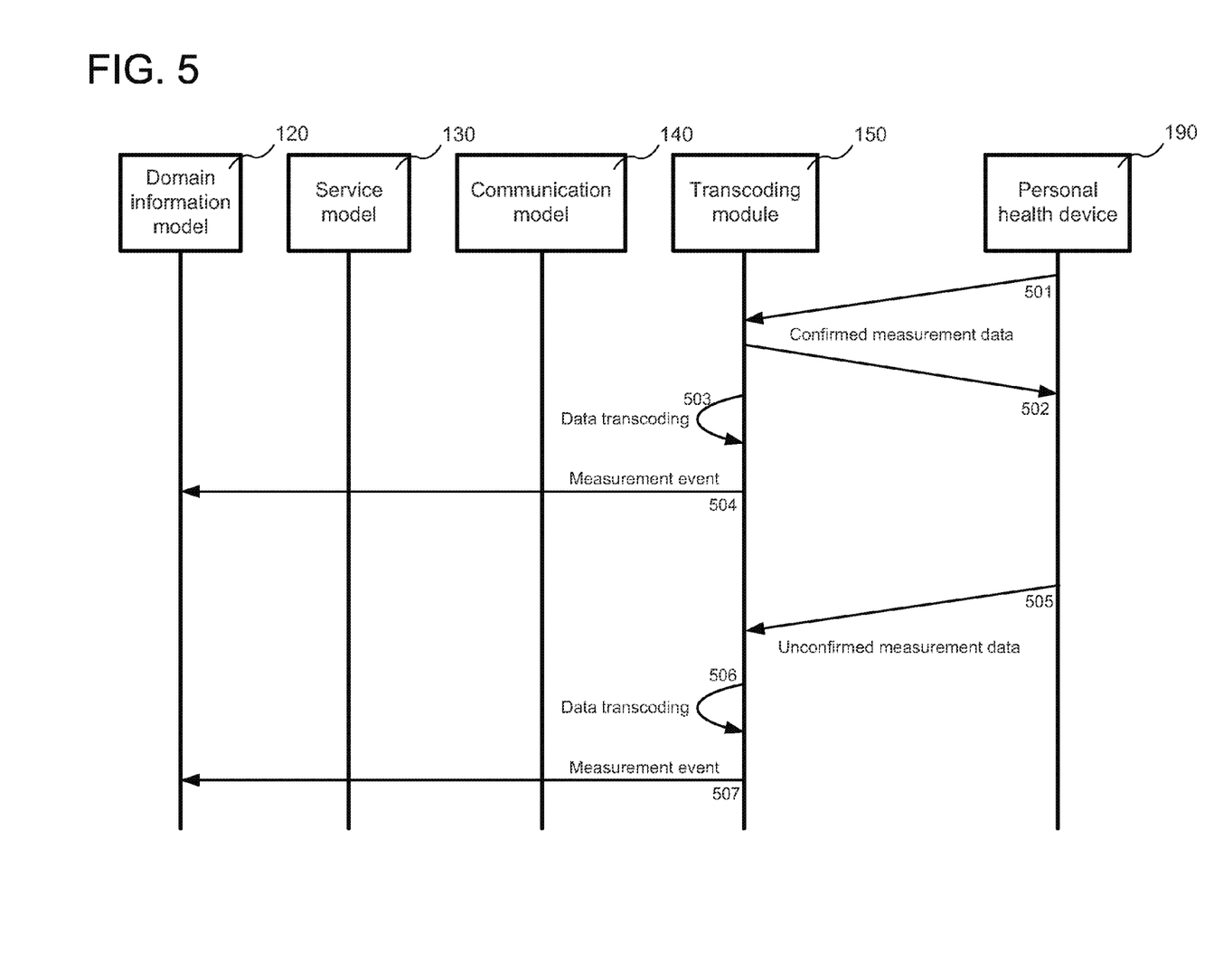
FIG. 5 illustrates example personal health device measurement data receipt processes, in accordance with various embodiments.

FIG. 5 illustrates example personal health device measurement data receipt processes, in accordance with various embodiments. In various embodiments, the actions illustrated in FIG. 5 may be performed by the transcoding module 150 and other actors in order to facilitate receipt of measurement data from the personal health device 190 by the manager device 100. In various embodiments, the action described in FIG. 5 may be merged, divided into other actions, and/or reordered.

In various embodiments, when measurement data comes from the personal health device, it may be transcoded and packaged in a suitable structure (such as, for example, ScanReportInfoFixed, SpanReportInfoVar, ScanReportInfoMPFixed, etc.). The transcoded and packaged measurement data may then be sent directly to the domain information model 120 of the stack 115. In various embodiments, the service model 130 may be bypassed.

In various embodiments, the transcoding module 150 may or may not confirm receipt of measurement data, such as through sending a acknowledgement to the personal health device 190. In various embodiments, the transcoding module 150 may send the acknowledgement based at least in part on whether and acknowledgement is expected by the personal health device 190.

Thus, in various embodiments, a measurement receipt process may begin at operation 501, where measurement data may be received from the personal health device 190. At operation 502, in various embodiments, the transcoding module 150 may confirm receipt of the measurement data by sending an acknowledgement back to the personal health device 190. As illustrated in FIG. 5, this acknowledgement may be performed before delivering the measurement data to the stack 115. Next, the transcoding module 150 may transcode the received measurement data at operation 503 and may deliver the transcoded data at operation 504. By contrast, operations 505, 506, and 507 illustrate similar actions performed when the personal health device does not require confirmation of measurement data receipt. Thus, at operation 505, measurement data may be received from the personal health device 190. Next, the transcoding module 150 may transcode the received measurement data at operation 506 and may deliver the transcoded data at operation 507. The process may then end.

In various embodiments, the personal health device 190 may be capable of storing measurements for later retrieval by the manager device 100. In various embodiments, the transcoding module 150 may be configured to transcode the stored data, which may allow the manager device 100 to access the stored measurement data using IEEE 11073 PM-Store service requests even if the personal health device 190 does not itself support such requests. In various embodiments, the transcoding module 150 may choose between two strategies regarding the store: 1) fetch on demand (asynchronously), or 2) fetch all stored data upon connection.

Figure 6:
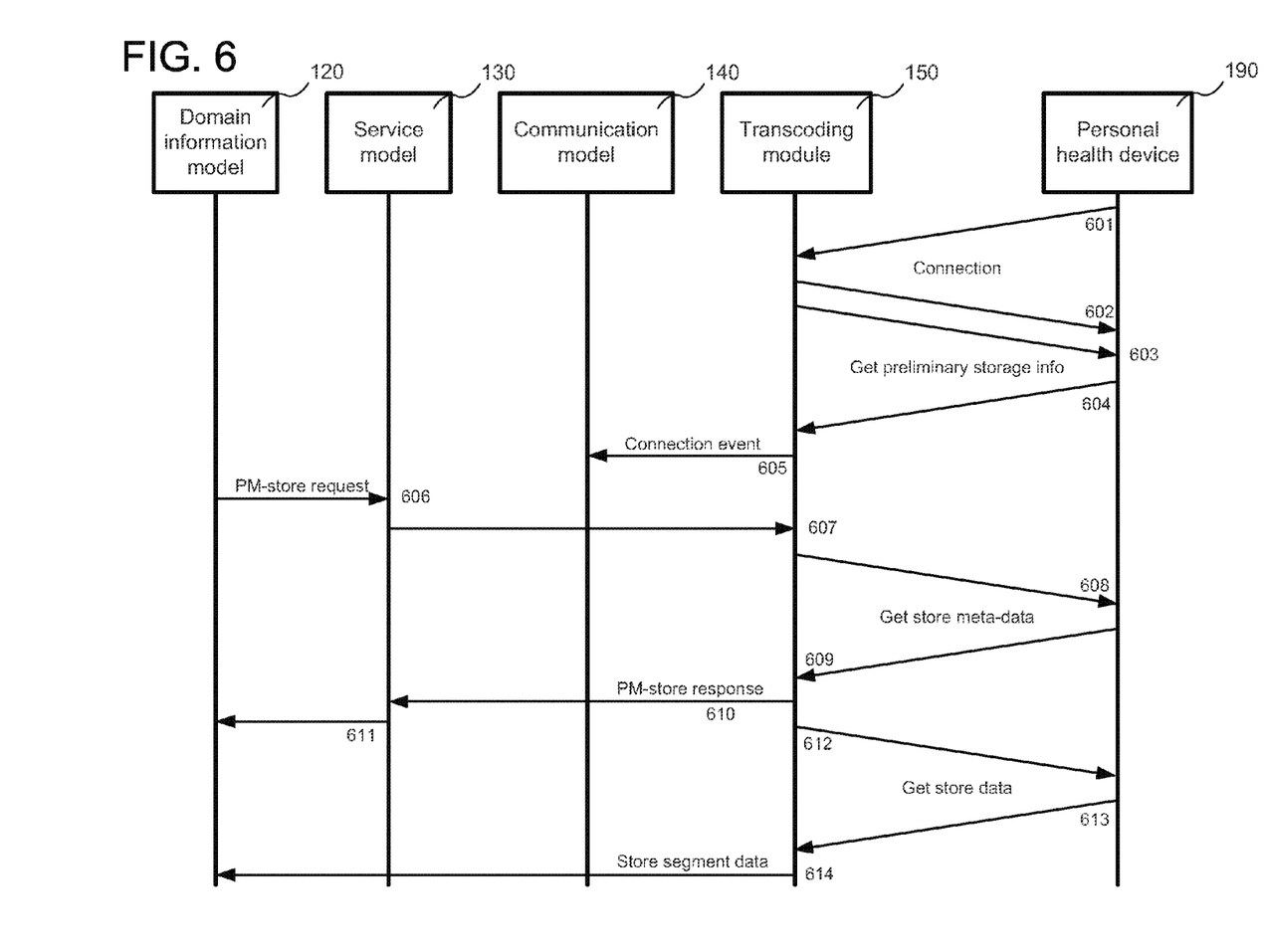
FIG. 6 illustrates an example personal health device stored data request and retrieval process, in accordance with various embodiments.

FIG. 6 illustrates an example personal health device stored data request and retrieval process, in accordance with various embodiments. In various embodiments, actions illustrated in FIG. 6 may be performed by the transcoding module 150 and other actors in order to facilitate an asynchronous retrieval of measurement data stored by the personal health device 190 by the manager device 100. In various embodiments, the action described in FIG. 6 may be merged, divided into other actions, and/or reordered.

The process may begin at operations 601 and 602, where, in various embodiments, a connection request may be received by the transcoding module from the personal health device 190 and the transcoding module 150 may establish the connection. Then, at operation 603, the transcoding module 150 may send a request to get preliminary storage info for the personal health device 190 and may receive preliminary storage information at operation 604. In various embodiments, the preliminary storage information may contain information about whether the personal health device 190 has storage capabilities and what type of storage it may perform. The request for and receipt of preliminary storage information may, in various embodiments, be performed before establishment of a connection for the personal health device 190 between the transcoding module 150 and the stack 115. Thus, at operation 605, the transcoding module 150 may then send a connection event to the communication model 140.

Next, at operation 606, in various embodiments, the domain information model 120 may send a PM-store Get request to the service model 130. At operation 607, the PM-store Get request may be intercepted by the transcoding module 150. Similarly to the discussion above, in various embodiments, the service model 130 may be configured to send the request to the transcoding module 150; in other embodiments, the transcoding module may intercept a request sent by the service model 130 to the communication model 140.

Next, at operation 608, the transcoding module 150 may get meta-data describing the store data that is to be sent from the personal storage device. In various embodiments, the transcoding module 150 may, at operation 608, transcode a GetSegmentInfo request from the stack 115, such as described above in the Set operation. In various embodiments, at operation 609 the personal health device 190 may respond with meta-data and/or summarized information for its stored data. The transcoding module 150 may then, at operation 610, provide a PM-store response to the service model 130, which may be sent to the domain information model at operation 611. In various embodiments, in the case of failure or receipt of bad parameters from the personal health device, a negative response may be provided to the stack 115 by the transcoding module 150.

Next, at operation 612, the transcoding module 150 may get stored data from the personal health device 190. In various embodiments, the transcoding module may be configured to transcode a TrigSegmDataXferReq request from the stack 115 to a data transfer request that may be understood by the personal health device 190, such as under similar guidelines as the Set operation. In various embodiments, the transcoding module may be configured to transcode the segment selection, and may provide a negative response in case of failure or bad parameters.

In various embodiments, at operation 613, the transcoding module 150 may receive segment data from the personal health device 190. Then, at operation 614, the transcoding module 150 may send segment data received by the transcoding module directly to the domain information model 120. In various embodiments, the transcoding module 150 may utilize the measurement data transcoding module 220 to encode and pass the information as a SegmentDataEvent structure. The process may then end.

Figure 7:
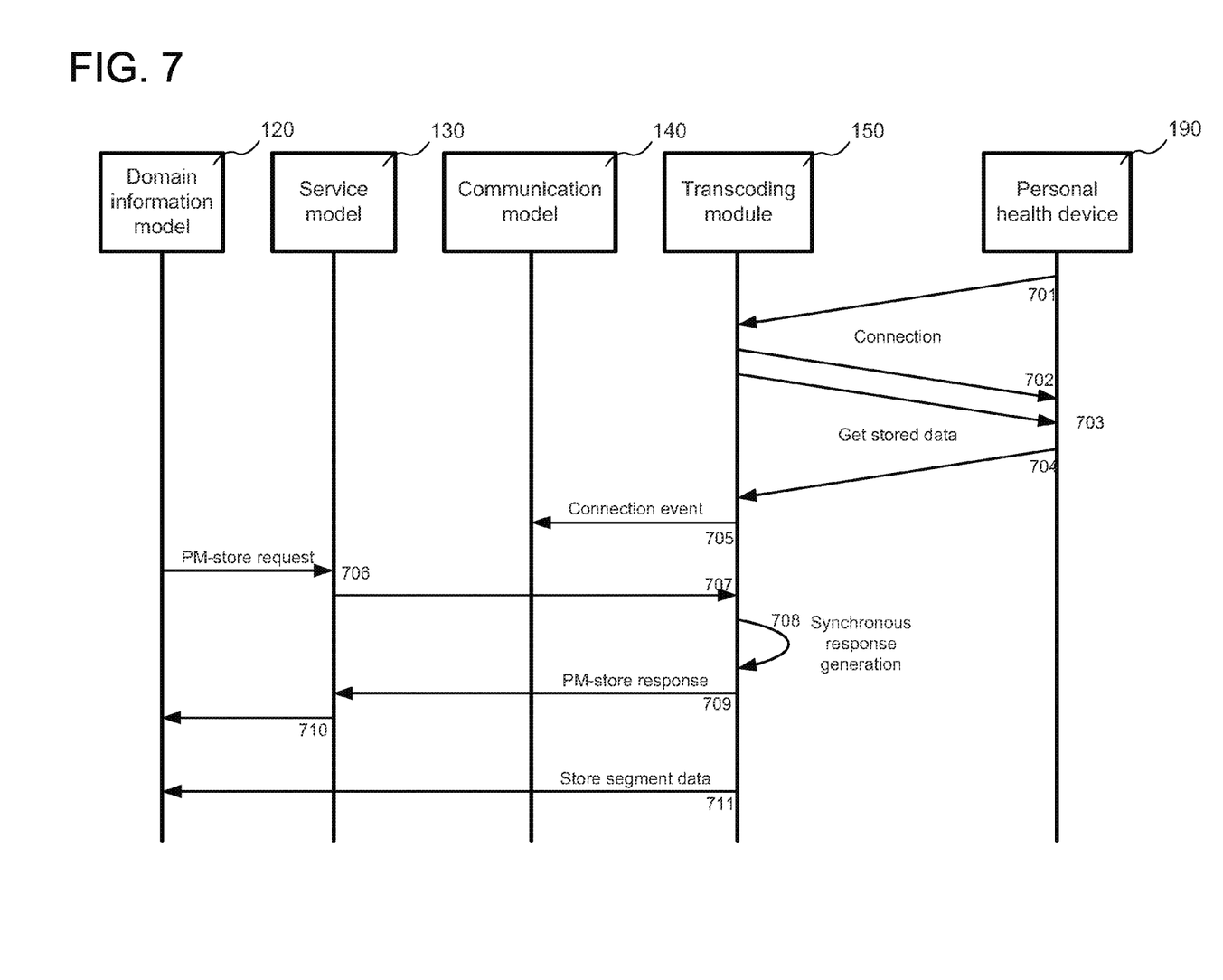
FIG. 7 illustrates another example personal health device stored data request and retrieval process, in accordance with various embodiments.

FIG. 7 illustrates a second example personal health device stored data request and retrieval process, in accordance with various embodiments. In various embodiments, actions illustrated in FIG. 7 may be performed by the transcoding module 150 and other actors in order to facilitate a synchronous retrieval of measurement data stored by the personal health device 190 by the manager device 100. In various embodiments, the action described in FIG. 7 may be merged, divided into other actions, and/or reordered.

The process may begin at operations 701 and 702, where, in various embodiments, a connection request may be received by the transcoding module from the personal health device 190 and the transcoding module 150 may establish the connection. Next, at operation 703, the transcoding module 150 may get stored data from the personal health device 190, and may receive the stored data at operation 704. In various embodiments, the transcoding module 150 may retrieve all or part of the data stored by the personal health device 190. In various embodiments, the stored data may be received prior to receipt of a PM-store request by the transcoding module 150; indeed, the transcoding module 150 may retrieve the stored data before even reporting a connection event to the stack 115. Thus, at operation 705, in various embodiments, the transcoding module 150 may send a connection event to the communication model 140 after retrieving the stored data from the personal health device 190.

Next, at operation 706, in various embodiments, the domain information model 120 may send a PM-store request to the service model 130. At operation 707, the PM-store request may be intercepted by the transcoding module 150. Similarly to the discussion above, in various embodiments, the service model 130 may be configured to send the request to the transcoding module 150; in other embodiments, the transcoding module may intercept a request sent by the service model 130 to the communication model 140.

At operation 708, the transcoding module 150 may generate a synchronous response using the previously-retrieved data from the personal health device 190. In various embodiments, the generation of the response may be done without further communication between the transcoding module 150 and the personal health device 190. The transcoding module 150 may then, at operation 709, provide a PM-store response to the service model 130, which may be sent to the domain information model at operation 710. In various embodiments, in the case of failure or receipt of bad parameters from the personal health device, a negative response may be provided to the stack 115 by the transcoding module 150. Then, at operation 711, the transcoding module 150 may send segment data retrieved by the transcoding module directly to the domain information model 120. In various embodiments, the transcoding module 150 may utilize the measurement data transcoding module 220 to encode and pass the information as a SegmentDataEvent structure. The process may then end.

Figure 8:
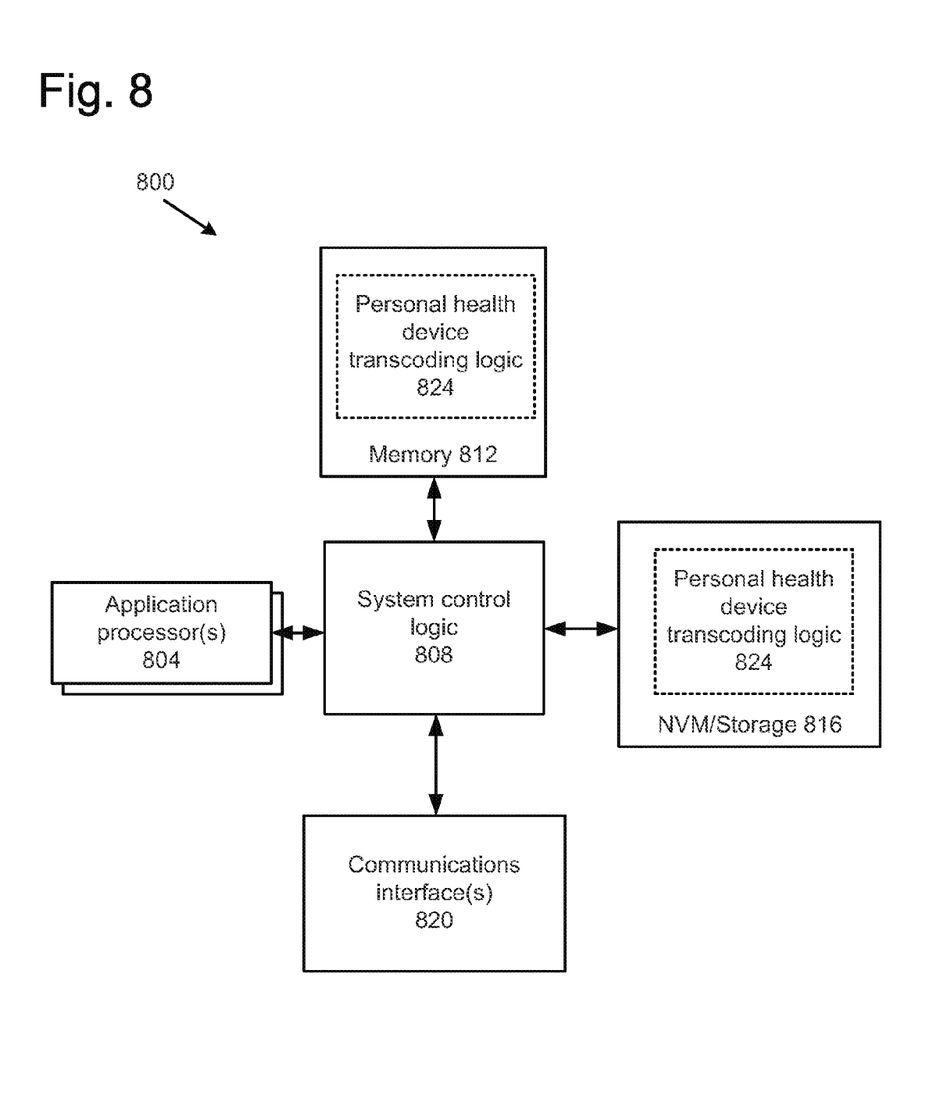
FIG. 8 illustrates an example computing environment suitable for practicing the disclosure, in accordance with various embodiments.

FIG. 8 illustrates, for one embodiment, an example computer system 800 suitable for practicing embodiments of the present disclosure. As illustrated, example computer system 800 may include control logic 808 coupled to at least one of the processor(s) 804, system memory 812 coupled to system control logic 808, non-volatile memory (NVM)/storage 816 coupled to system control logic 808, and one or more communications interface(s) 820 coupled to system control logic 808. In various embodiments, the one or more processors 804 may be a processor core.

System control logic 808 for one embodiment may include any suitable interface controllers to provide for any suitable interface to at least one of the processor(s) 804 and/or to any suitable device or component in communication with system control logic 808.

System control logic 808 for one embodiment may include one or more memory controller(s) to provide an interface to system memory 812. System memory 812 may be used to load and store data and/or instructions, for example, for system 800. In one embodiment, system memory 812 may include any suitable volatile memory, such as suitable dynamic random access memory ("DRAM"), for example.

System control logic 808, in one embodiment, may include one or more input/output ("I/O") controller(s) to provide an interface to NVM/storage 816 and communications interface(s) 820.

NVM/storage 816 may be used to store data and/or instructions, for example. NVM/storage 816 may include any suitable non-volatile memory, such as flash memory, for example, and/or may include any suitable non-volatile storage device(s), such as one or more hard disk drive(s) ("HDD(s)"), one or more solid-state drive(s), one or more compact disc ("CD") drive(s), and/or one or more digital versatile disc ("DVD") drive(s), for example.

The NVM/storage 816 may include a storage resource physically part of a device on which the system 800 is installed or it may be accessible by, but not necessarily a part of, the device. For example, the NVM/storage 816 may be accessed over a network via the communications interface(s) 820.

System memory 812 and NVM/storage 816 may include, in particular, temporal and persistent copies of personal health device transcoding logic 824. The personal health device transcoding logic 824 may include instructions that when executed by at least one of the processor(s) 804 result in the system 800 practicing one or more of the operations described above for the transcoding module 150. In some embodiments, the personal health device transcoding logic 824 may additionally/alternatively be located in the system control logic 808.

Communications interface(s) 820 may provide an interface for system 800 to communicate over one or more network(s) and/or with any other suitable device. Communications interface(s) 820 may include any suitable hardware and/or firmware, such as a network adapter, one or more antennas, a wireless interface, and so forth. In various embodiments, communication interface(s) 820 may include an interface for system 800 to use NFC, optical communications (e.g., barcodes), Bluetooth or other similar technologies to communicate directly (e.g., without an intermediary) with another device.

For one embodiment, at least one of the processor(s) 804 may be packaged together with system control logic 808 and/or personal health device transcoding logic 824 (in whole or in part). For one embodiment, at least one of the processor(s) 804 may be packaged together with system control logic 808 and/or personal health device transcoding logic 824 (in whole or in part) to form a System in Package ("SiP"). For one embodiment, at least one of the processor(s) 804 may be integrated on the same die with system control logic 808 and/or personal health device transcoding logic 824 (in whole or in part). For one embodiment, at least one of the processor(s) 804 may be integrated on the same die with system control logic 808 and/or personal health device transcoding logic 824 (in whole or in part) to form a System on Chip ("SoC").

In various embodiments, a computer-implemented method may facilitate communications between a personal health device and a manager device, which may be configured to implement a stack of health information protocols. The method may include redirecting, by a transcoding module executing on a computing device, a communication to be sent between the manager device and the personal health device via the stack of health information protocols, such that the communication is not sent through the entire stack of health information protocols. The method may also include emulating, by the transcoding module, transmission of the communication to the personal health device. The method may also include emulating, by the transcoding module, transmission of one or more responses from the personal health device to the manager device such that the one or more responses appear, to the manager device, to be generated by the personal health device through implementing the stack of health information protocols.

In various embodiments, the transcoding module may be executed on the manager device and redirecting the communication may include redirecting the communication before it is sent outside of the manager device. In various embodiments, the stack of health information protocols may include an IEEE 11073-20601 standard stack (IEEE stack) and the manager device may include an IEEE 11073-20601-compliant manager device.

In various embodiments, emulating transmission of one or more responses may include providing the one or more responses directly into the IEEE stack at a domain information model level or a service model level. In various embodiments, redirecting the communication may include: redirecting the communication from the IEEE stack at a domain information model level or a service model level, transcoding the redirected communication such that it may be understood by the personal health device, and transmitting the transcoded communication to the personal health device via a communication channel.

In various embodiments, wherein emulating transmission of one or more responses may include generating information, by the transcoding module, that appears to the manager device to be generated by the personal health device through implementation of the IEEE stack and providing, by the transcoding module, the generated information to the IEEE stack.

In various embodiments, generating information may include generating a IEEE 11073-20601 standard-compliant medical device system object describing the personal health device. In various embodiments, generating information may include generating an IEEE 11073-20601 standard-compliant connection event and providing the generated information comprises providing the connection event to a communication model of the IEEE stack. In various embodiments, generating information may include: receiving information generated by the personal health device and transcoding the received information such that the transcoded information appears to be generated through implementation of the IEEE stack by the personal health device.

In various embodiments, emulating transmission of one or more responses may include: requesting information from the personal health device prior to a request of the information from the IEEE stack, storing the requested information, and in response to a subsequent request for the information, providing the stored information to the IEEE stack.

In various embodiments, the method may further include communicating with the personal health device via a protocol that is other than the stack of health information protocols.

In various embodiments, an IEEE 11073-20601 standard-compliant manager device may include one or more computer processors. The manager device may also include one or more stack modules configured to be operated on the one or more computer processors to implement a IEEE 11073-20601 standard stack (IEEE stack) to communicate with a personal health device that implements the IEEE 11073-20601 standard stack. The manager device may also include a transcoder module configured to be operated on the one or more computer processors. The transcoder module may be configured to redirect a communication to be sent through the IEEE stack from the manager device to a personal health device such that the communication is not sent through the entire IEEE stack. The transcoder module may also be configured to emulate transmission of the communication to the personal health device. The transcoder module may also be configured to emulate transmission of one or more responses from the personal health device to the IEEE stack such that the personal health device appears to implement the IEEE stack.

In various embodiments, the transcoder module may be configured to redirect the communication and to emulate transmission of one or more responses directly with the IEEE stack at a domain information model level or a service model level.

In various embodiments, emulate transmission of one or more responses may include generate information that appears to be generated by the personal health device through implementation of an IEEE stack at the personal health device and provide the generated information to the IEEE stack at the manager device.

In various embodiments, generate information may include generate an IEEE 11073-20601 standard-compliant medical device system object describing the personal health device or an IEEE 11073-20601 standard-compliant connection event. In various embodiments, generate information may include receive information generated by the personal health device and transcode the received information such that the transcoded information appears to be generated through implementation of an IEEE stack at the personal health device.

Computer-readable media (including non-transitory computer-readable media), methods, apparatuses, systems and devices for performing the above-described techniques are illustrative examples of embodiments disclosed herein. Additionally, other devices in the above-described interactions may be configured to perform various disclosed techniques.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

What is claimed is:
1. A computer-implemented method for facilitating communications between a personal health device and a manager device, the manager device configured to implement a stack of health information protocols, the method comprising;
redirecting, by a transcoding module executing on a computing device, a communication to be sent between the manager device and the personal health device via the stack of health information protocols, such that the communication is not sent through the entire stack of health information protocols;
emulating, by the transcoding module, transmission of the communication to the personal health device; and
emulating, by the transcoding module, transmission of one or more responses from the personal health device to the manager device such that the one or more responses appear, to the manager device, to be generated by the personal health device through implementing the stack of health information protocols;
wherein emulating transmission of one or more responses comprises:
requesting information from the personal health device prior to a request for the information from the manager device;
storing the requested information; and
in response to a subsequent request for the information, providing the stored information to the manager device.

2. The method of claim 1, wherein:
the transcoding module is executed on the manager device; and
redirecting the communication comprises redirecting the communication before it is sent outside of the manager device.

3. The method of claim 1, wherein:
the stack of health information protocols comprises an IEEE 11073-20601 standard stack (IEEE stack); and
the manager device comprises an IEEE 11073-20601-compliant manager device.

4. The method of claim 3, wherein emulating transmission of one or more responses comprises providing the one or more responses directly into the IEEE stack at a domain information model level or a service model level.

5. The method of claim 3, wherein redirecting the communication comprises:
redirecting the communication from the IEEE stack at a domain information model level or a service model level;
transcoding the redirected communication such that it may be understood by the personal health device; and
transmitting the transcoded communication to the personal health device via a communication channel.

6. The method of claim 3, wherein emulating transmission of one or more responses comprises:
generating information, by the transcoding module, that appears to the manager device to be generated by the personal health device through implementation of the IEEE stack; and
providing, by the transcoding module, the generated information to the IEEE stack.

7. The method of claim 6, wherein generating information comprises generating a IEEE 11073-20601 standard-compliant medical device system object describing the personal health device.

8. The method of claim 6, wherein generating information comprises generating an IEEE 11073-20601 standard-compliant connection event and providing the generated information comprises providing the connection event to a communication model of the IEEE stack.

9. The method of claim 6, wherein generating information comprises:
    receiving information generated by the personal health device; and
    transcoding the received information such that the transcoded information appears to be generated through implementation of the IEEE stack by the personal health device.

10. The method of claim 1, further comprising communicating with the personal health device via a protocol that is other than the stack of health information protocols.

11. An IEEE 11073-20601 standard-compliant manager device, comprising:
    one or more computer processors;
    one or more stack modules configured to be operated on the one or more computer processors to implement a IEEE 11073-20601 standard stack (IEEE stack) to communicate with a personal health device that does not implement the IEEE 11073-20601 standard stack; and
    a transcoder module configured to be operated on the one or more computer processors to:
        redirect a communication to be sent through the IEEE stack from the manager device to a personal health device such that the communication is not sent through the entire IEEE stack;
        emulate transmission of the communication to the personal health device; and
        emulate transmission of one or more responses from the personal health device to the IEEE stack such that the personal health device appears to implement the IEEE stack, including request information from the personal health device prior to a request for the information from the IEEE stack, store the requested information, and, in response to a subsequent request for the information, provide the stored information to the IEEE stack.

12. The device of claim 11, wherein the transcoder module is configured to redirect the communication and to emulate transmission of one or more responses directly with the IEEE stack at a domain information model level or a service model level.

13. The device of claim 11, wherein emulate transmission of one or more responses comprises:
    generate information that appears to be generated by the personal health device through implementation of an IEEE stack at the personal health device; and
    provide the generated information to the IEEE stack at the manager device.

14. The device of claim 13, wherein generate information comprises generate an IEEE 11073-20601 standard-compliant medical device system object describing the personal health device or an IEEE 11073-20601 standard-compliant connection event.

15. The device of claim 13, wherein generate information comprises:
    receive information generated by the personal health device; and
    transcode the received information such that the transcoded information appears to be generated through implementation of an IEEE stack at the personal health device.

16. One or more non-transitory computer-readable media comprising instructions stored thereon that are configured to be executed on a manager computing device that implements a IEEE 11073-20601 standard stack (IEEE stack), wherein the instructions are configured to cause the manager device, in response to execution of the instructions, to:
    redirect a communication to be sent through the IEEE stack from the manager device to a personal health device such that the communication is not sent through the entire IEEE stack;
    emulate transmission of the communication to the personal health device; and
    emulate transmission of one or more responses from the personal health device to the IEEE stack such that the personal health device appears to implement the IEEE stack, wherein emulate transmission of one or more responses comprises:
        request information from the personal health device prior to a request for the information from the IEEE stack;
        store the requested information; and
        in response to a subsequent request for the information, provide the stored information to the IEEE stack.

17. The non-transitory computer-readable media of claim 16, wherein the instructions are configured to cause the manager device to redirect the communication and to emulate transmission of one or more responses directly with the IEEE stack at a domain information model level or a service model level.

18. The non-transitory computer-readable media of claim 16, wherein the instructions are configured to emulate transmission of one or more responses through:
    generation of information that appears to be generated by the personal health device through implementation of an IEEE stack at the personal health device; and
    provision of the generated information to the IEEE stack at the manager device.

19. The non-transitory computer-readable media of claim 18, wherein generation of information comprises generation of an IEEE 11073-20601 standard-compliant medical device system object describing the personal health device or an IEEE 11073-20601 standard-compliant connection event.

* * * * *